United States Patent [19]

Biller

[11] 4,393,239

[45] Jul. 12, 1983

[54] PROCESS FOR THE PREPARATION OF POLYARYL AMINES HAVING METHYLENE BRIDGES

[75] Inventor: Efim Biller, Zürich, Switzerland

[73] Assignee: Elprochine AG, Zurich, Switzerland

[21] Appl. No.: 140,914

[22] Filed: Apr. 16, 1980

Related U.S. Application Data

[63] Continuation of Ser. No. 2,812, Jan. 11, 1979, abandoned, which is a continuation of Ser. No. 847,650, Nov. 1, 1977, abandoned.

[30] Foreign Application Priority Data

Nov. 6, 1976 [CH] Switzerland .................. 14012/76

[51] Int. Cl.³ ............................................ C07C 85/08
[52] U.S. Cl. ............................ 564/331; 260/453 PH; 260/453 AM; 260/501.16; 260/501.21; 564/333
[58] Field of Search .................. 260/570 D; 564/331, 564/333

[56] References Cited

U.S. PATENT DOCUMENTS

| | | | |
|---|---|---|---|
| 3,297,759 | 1/1967 | Curtis et al. | 260/570 |
| 3,367,969 | 2/1968 | Perkins | 260/570 |
| 3,857,890 | 12/1974 | Recchia | 260/570 |
| 3,996,283 | 12/1976 | Korofel | 260/570 |

*Primary Examiner*—Robert V. Hines
*Attorney, Agent, or Firm*—Sprung, Horn, Kramer & Woods

[57] ABSTRACT

A process has been invented for the preparation of polyaryl polyamines having methylene bridges by condensation of primary arylamines with formaldehyde in the presence of a catalyst. According to the invention, the amount of binuclear compounds and an improved viscosity can be obtained if one adds the remaining amount of primary arylamine immediately after the formaldehyde.

4 Claims, No Drawings

PROCESS FOR THE PREPARATION OF POLYARYL AMINES HAVING METHYLENE BRIDGES

This is a continuation of application Ser. No. 002,812 filed Jan. 11, 1979 now abandoned, which in turn became a continuation of Ser. No. 847,650 filed Nov. 1, 1977, now abandoned.

This invention concerns the preparation of polyaryl polyamines having methylene bridges by condensation of primary arylamines with formaldehyde in the presence of a catalyst.

The preparation of polyaryl amines having methylene bridges, as well as the conversion of those compounds into corresponding methylene-bridge-containing polyphenyl polyisocyanates is generally known. The polyisocyanates are frequently used as intermediate products in the production of polyurethanes in the form of, for instance, hard foams, molded plastic products and elastomers and also as source of the simplest polyarylpolyisocyanate having methylene bridges, the pure diaryl methane diisocyanate.

The proportion of the monomers, i.e., of the diamines, the triamines, the tetramines, and so on, can be influenced by the modification of the proportion of aniline to formaldehyde and of the aniline to acid catalyst concentration, as well as of the temperature of the addition of the formaldehyde. Other important factors regarding the reaction are the temperature of the final rearrangement and the time of the reaction.

It is desirable that polyphenyl polyisocyanates having methylene bridges, prepared from the above amine compositions and used for the preparation of foamed polyurethanes, i.e., especially of hard foamed polyurethanes, have a high isocyanate content, are moderately viscous and contain a considerable amount of isocyanates with a functionality higher than two.

Polyaryl amines having intermediate methylene bridges, which contain substantial amounts of tri-, tetra- and higher polyamines, can be obtained if one uses low aniline proportions, and to a small extent also if one uses low proportions of acid per mol of formaldehyde, e.g., if one uses 1.4 to 1.9 mol of aniline and 0.4 to 0.7 mol of acid per mol of formaldehyde.

Products having a higher content of monomer can be obtained if one works, for instance, with high turbulence (German Pat. No. 1,643,363 or DOS No. 2,049,707). The two processes require the conducting of the reaction at least partially (German Pat. No. 1,643,363) or totally in a current with high turbulence or without remixing. Tube reactors are required for this which have great lengths at minimum diameter and are pressure-stressed because of the high viscosities and speeds.

Also known is a process provided in U.S. Pat. No. 3,367,969, according to which the formation of monomers is favored by two-stage aniline addition. Accordingly, aniline with formaldehyde is kept, in the presence of hydrochloric acid, at 20° to 50° C. long enough for the reaction to be virtually complete. One then adds the remaining aniline and completes the reaction at 50° to 100° C. This means that the originally formed compounds of the anhydroformaldehyde aniline type are first reacted to form benzyl anilines before the remaining aniline is added.

Surprisingly, it has now been discovered that the amount of the binuclear compounds and an improved viscosity can be obtained if one adds the remaining aniline immediately after the formaldehyde.

This is probably due to the fact that the transcondensation of the originally formed compounds of the anhydroformaldehyde aniline or azomethine type favorably influences the reaction with freshly added aniline in the direction of the formation of binuclear compounds.

It also became evident that it is also of advantage to add the free aniline totally or partially simultaneously with formaldehyde to the aqueous salt solution. Also in this case the reaction mixture remains virtually homogeneous and the proportion of diamine increases further.

If products with a higher diamine content (over 70%) are to be prepared, then the acid addition (free or as salt) can take place in two stages. In this case, the acid residue is also added with the residual aniline amount.

The process according to the instant invention makes it possible to produce, with reduced introduction of catalyst, as good or better products than is possible according to the prior art.

The solubility of arylamine sulfonic acid salts in water is relatively poor. It has now been found that additions of trifluoroacetic acid rapidly reduce the crystallization points of the salt solutions. A salt mixture having 25% trifluoroacetic acid reduces the crystallization point to approximately 35° C. A 50/50% salt solution remains liquid at room temperature. Also important is the fact that these salt solutions do not attack chrome-nickel steel.

The arylamines used in the invention are particularly monocyclic carbocyclic aryl amines, especially aniline.

EXAMPLE 1

93 g of aniline (1 mol), 96 g of methane sulfonic acid (1 mol) and 150 g water are placed into a double-walled vessel with stirrer and reflux cooler with connected thermostat, homogenized at 75° C. and cooled to 47° C., a crystal sludge resulting. Then 81 g of 37% (1 mol) formaldehyde are dropped in under intensive guidance within fifteen minutes at approximately 47°/48° C. Immediately after the completion of the formaldehyde addition, an additional 93 g (1 mol) of aniline are added. The solution remains virtually homogeneous.

Then it is kept for:
1 hour at 50° C., then for
1 hour at 70° C., and finally
1.5 hours at 90° C.

The working up is effected by neutralization with NaOH and water washing at 80° C.:

The sediment corresponds to a mol ratio of aniline/formaldehyde/acid of 2.0:1:1.

The GPC analysis yields a content of 66% of diamine (MDA).

EXAMPLE 2

The procedure of Example 1 is followed except that the addition of the free aniline is effected in a manner analagous to U.S. Pat. No. 3,367,969, i.e., thirty minutes after the termination of the formaldehyde addition.

Then it is kept for:
0.5 hour at 50° C., then for
1 hour at 70° C., and finally
1.5 hours at 90° C.

and worked up as in Example 1 and examined.

MDA content 51%.

EXAMPLE 3

The procedure of Example 1 is followed except that the addition of the free aniline is effected in a manner analagous to U.S. Pat. No. 3,367,969, i.e., 60 minutes after the termination of the formaldehyde addition.

Then it is kept for:
1 hour at 70° C., and then for
1.5 hours at 90° C.
and worked up as in Example 1 and examined.
MDA content 44%.

EXAMPLES 4 AND 5

93 g of aniline (1 mol), 48 g of methane sulfonic acid (0.5 mol), 57 g of trifluoroacetic acid (0.5 mol) and 162 g of water each time are placed into two double-walled vessels with stirrer connected with a joint thermostat. There result solutions which remain homogeneous at 30° C.

Finally, within a period of 15 minutes at a temperature of about 35°–40° C., 81 g of formaldehyde 37% (1 mol) are added dropwise under intensive stirring. The additional aniline, 74 g (0.8 mol) in Test 4 and 56 g (0.6 mol) in Test 5, are added virtually simultaneously with the last third of the formaldehyde.

The sediments have the following mol ratios:

| | Aniline/formaldehyde/acid |
|---|---|
| Test 4 | 1.8:1:1 |
| Test 5 | 1.6:1:1 |

Then, working up is effected as in Example 1 and examines with GLC as well as with GPC.

| Test | 4-4 Isomer In Dimer | Dimer | Trimer | Higher Molecular Polyaryl Polyam |
|---|---|---|---|---|
| 4 | 98.1% | 62 | 23 | 15 |
| 5 | 99.5% | 39 | 24 | 38 |

What is claimed is:

1. In a process for the preparation of polyaryl amines having methylene bridges from arylamines and formaldehyde in the presence of acids wherein 0.25–1.3 mol of formaldehyde per mol of arylamine is added in a first mixing step in the presence of 0.85–1.01 mol of acid, the improvement which comprises adding at least 0.1 mol of free arylamine before the formed compounds of the anhydroformaldehyde aniline type are noticeably rearranged into benzyl anilines, then reacting the reaction mixture at temperatures between 30° and 70° C. to form benzyl anilines and, finally, converting the resulting precondensate at temperatures between 70° and 120° C. into polyamines having methylene bridges.

2. A process according to claim 1, wherein a portion of the acid is added simultaneously with free arylamine as free acid or salt.

3. A process according to claim 1, wherein the acid is methane sulfonic acid and trifluoro acetic acid.

4. A process according to claim 1, wherein the arylamine is aniline.

* * * * *